United States Patent [19]
Homola et al.

[11] Patent Number: 5,980,868
[45] Date of Patent: *Nov. 9, 1999

[54] METHODS, COMPOSITIONS, AND DENTAL DELIVERY SYSTEMS FOR THE PROTECTION OF THE SURFACES OF TEETH

[76] Inventors: Andrew M. Homola, 16823 Sorrel Way, Morgan Hill, Calif. 95037; Ronald K. Dunton, 40 Highgate Rd., Santa Cruz, Calif. 95066

[ * ] Notice: This patent issued on a continued prosecution application filed under 37 CFR 1.53(d), and is subject to the twenty year patent term provisions of 35 U.S.C. 154(a)(2).

[21] Appl. No.: 08/620,361

[22] Filed: Mar. 22, 1996

Related U.S. Application Data

[62] Division of application No. 08/373,946, Jan. 17, 1995, abandoned.

[51] Int. Cl.⁶ .............. A61K 7/22; A61C 15/00; A46B 9/04; C09K 3/00
[52] U.S. Cl. .................. 424/54; 424/49; 424/52; 424/401; 15/167.1; 106/35; 132/321; 433/215; 433/217.1
[58] Field of Search .............. 424/49, 54; 106/35; 132/321; 433/215, 217.1

[56] References Cited

U.S. PATENT DOCUMENTS

| | | |
|---|---|---|
| Re. 31,787 | 1/1985 | Chang . |
| 2,684,924 | 7/1954 | Rose et al. . |
| 2,984,639 | 5/1961 | Stamberger et al. . |
| 2,990,425 | 7/1961 | Senior . |
| 3,183,230 | 5/1965 | Shapiro et al. . |
| 3,325,402 | 6/1967 | Mortimer . |
| 3,431,208 | 3/1969 | Bailey . |
| 3,468,898 | 9/1969 | Cutler et al. . |
| 3,703,583 | 11/1972 | Martin . |
| 3,862,308 | 1/1975 | Schmitt et al. ............ 424/54 |
| 4,020,019 | 4/1977 | Soldati et al. ............ 260/2 |
| 4,022,834 | 5/1977 | Gundersen . |
| 4,029,113 | 6/1977 | Guyton ............ 132/91 |
| 4,053,636 | 10/1977 | Eustis, III et al. . |
| 4,102,827 | 7/1978 | Rembaum et al. ............ 260/823 |
| 4,157,386 | 6/1979 | La Rochelle . |
| 4,169,885 | 10/1979 | Raaf et al. . |
| 4,198,425 | 4/1980 | Mitsui et al. . |
| 4,428,930 | 1/1984 | Chang ............ 424/52 |
| 4,485,090 | 11/1984 | Chang ............ 424/52 |
| 4,490,353 | 12/1984 | Crawford et al. . |
| 4,504,228 | 3/1985 | Maetani et al. . |
| 4,528,182 | 7/1985 | Curtis et al. . |
| 4,776,358 | 10/1988 | Lorch . |
| 4,996,056 | 2/1991 | Blass . |
| 5,033,488 | 7/1991 | Curtis et al. ............ 132/321 |
| 5,165,913 | 11/1992 | Hill et al. . |
| 5,174,313 | 12/1992 | Rosenberger ............ 132/321 |
| 5,209,251 | 5/1993 | Curtis et al. ............ 132/321 |
| 5,290,541 | 3/1994 | Liang . |
| 5,320,842 | 6/1994 | Spencer ............ 424/401 |
| 5,340,581 | 8/1994 | Tseng et al. ............ 424/401 |
| 5,344,641 | 9/1994 | Gaffar et al. . |

FOREIGN PATENT DOCUMENTS

| | | |
|---|---|---|
| 0 026 539 | 4/1981 | European Pat. Off. . |
| 0 049 830 | 4/1982 | European Pat. Off. . |
| 0 451 972 | 10/1991 | European Pat. Off. . |
| 26 26 935 | 12/1977 | Germany . |
| 29 25 020 | 1/1981 | Germany . |
| 1 251 904 | 8/1986 | Russian Federation . |
| 1 319 396 | 6/1973 | United Kingdom . |
| 1319396 | 6/1973 | United Kingdom . |
| 2 001 526 | 2/1979 | United Kingdom . |
| WO 89/11848 | 12/1989 | WIPO . |
| WO 90/15591 | 12/1990 | WIPO . |
| WO 93/20775 | 10/1993 | WIPO . |

OTHER PUBLICATIONS

R. Wunderlish et al, *J. Dent. Res.,* vol. 60A, "The Effect of Waxed and Unwaxed Dental Floss on Gingival Response", Abstract No. 862, p. 525, (1981).
P. Finkelstein et al, *J. Dent. Res.,* vol. 58, No. 3, pp. 1034–1039, "The Effectiveness of Dental Floss in Reducing Gingival Inflammation", (1979).
Dunton et al WO/PCT 93/20,775 Oct. 28, 1993.
Beggs et al EP 451972 Oct. 16, 1991.
Aleksina et al USSR 1251904 Aug. 23, 1986.
Derinelli Ger DE 2925020 Jan. 8, 1981.
Dana (I) WO/PCT 90 15591 Dec. 27, 1990 DANA (II) WO/PCT 89/11848 Dec. 14, 1989.
Muhlemann et al (I) E.P. 49830 Apr. 21, 1982 Muehlmann et al (II) EP 26539 Apr. 8, 1981.
Cannell Brit UK GB 2001526 Feb. 7, 1979.
Kunz et al Ger DE 2626935 Dec. 29, 1977.
*Journal of the American Dental Association,* (Sep. 1967), 75, No. 3, pp. 638–644, "Clinical Anticaries Effect of Repeated Topical Sodium Fluoride Applications by Mouthpieces", H. Englander et al.

*Primary Examiner*—Shep K. Rose
*Attorney, Agent, or Firm*—Oblon, Spivak, McClelland, Maier & Neustadt, P.C.

[57] ABSTRACT

The present invention discloses applicators containing cationic surface active agents, hydrophobic barrier-forming materials and antimicrobial compounds which form, upon application to dental surfaces, a protective and bacteria-inhibiting film.

18 Claims, 9 Drawing Sheets

METHODS, COMPOSITIONS, AND DENTAL DELIVERY SYSTEMS FOR THE PROTECTION OF THE SURFACES OF TEETH

This is a Division, of application Ser. No. 08/373,946 filed on Jan. 17, 1995, now abandoned.

BACKGROUND OF THE INVENTION

1. Field of the Invention

The present invention relates to oral hygiene and specifically to methods of treating the oral cavity with a dental delivery system, such as a dental floss or toothpick, with improved cleaning, conditioning and antimicrobial properties, which provides the teeth with an impervious protective barrier. The present invention also relates to compositions and dental delivery systems having improved cleaning, conditioning, and antimicrobial properties, which provide the teeth with an impervious protective barrier. The present invention also relates to novel cationic surfactants especially suited for use in the present compositions, methods, and dental delivery systems.

2. Description of the Background

The oral care industry and health research communities have looked for many years for a way to interdict the attachment, propagation, growth or colonization of bacteria on teeth since adhered bacteria are the start of a pernicious chain of events leading to formation of home care-resistant plaque, calculus, and ultimately, tooth-loss. As people in developed countries live longer, dental care plays a larger role in overall health, and developing countries are becoming more aware of the importance of oral hygiene.

Dental plaque results when cariogenic bacteria (e.g., *Streptococcus mutans*) collect in colonies and form deposits on tooth surfaces. The presence of the bacteria and deposits is extremely detrimental to the health of the tooth for, if left unchecked, they may result in infected gingival tissue, the formation of dental caries and possibly periodontal disease. In extreme cases their presence may even result in the loss of teeth. Many attempts have been made to control or prevent both the occurrence of dental caries and the formation of dental plaque. For example, fluoride solutions or gels have been used. Treatment with these materials is typically performed in a dental office at periodic, but not frequent, intervals. Such treatments are primarily intended to render tooth enamel more resistant to the acid action caused by plaque. They do not, however, result in plaque control for an extended period since plaque reestablishes itself on the teeth shortly after ingestion of food.

Even when the frequency of application of such solutions and gels is increased only partial control has been shown. For example, studies wherein a fluoride-containing solution (1% fluoride concentration) was applied four to five times in the course of a year have demonstrated that this technique had only limited success due to the rapid reestablishment of plaque in the oral cavity. Moreover, the daily application of a fluoride gel by means of a custom-fitted polyvinyl mouthpiece for a period of twenty-one months also showed no substantial change in plaque formation among treated and untreated patients (see "Clinical Anticaries Effect of A Repeated Sodium Fluoride Application by Mouthpiece," *Journal of the American Dental Association*, vol. 75, no. 3, September, 1967, pages 638–644).

Proper use of dental floss is necessary to clean the considerable area on the interproximal surfaces of teeth, which cannot be reached by the bristles of a toothbrush.

The purpose of using dental floss is:
1. to dislodge and remove any decomposing food material that has accumulated at the interproximal surfaces that cannot be removed by brushing; and
2. to dislodge and remove as much as possible the growth of bacterial material (plaque) upon the teeth or the superimposed calculus that has accumulated there since the previous cleaning.

The concept of the use of dental floss for cleansing interproximal spaces appears to have been introduced by Parmly in 1819 ("Practical Guide to the Management of the Teeth," Collins & Croft, Philadelphia Pa.). Parmly suggested the use of waxed silk to clean teeth of persons subject to gingival inflammation. Numerous types of floss were developed and used for cleaning, until finally in 1948 Bass established the optimum characteristics of dental floss (*Dental Items of Interest*, vol. 70, pp. 921–34, (1948)). Most floss sold at retail today is also "waxed" to assist penetration to interproximal regions; as the "cord" effect described by Bass makes the floss bundle difficult to force between closely spaced teeth.

From 1960 through 1962, numerous clinical studies reported that there is no clinical difference as to plaque removal and gingivitis scores between waxed and unwaxed dental floss. O'Leary in 1970, and Hill et al. in 1973, found no difference in the interproximal cleansing properties of waxed or unwaxed dental floss. This was reconfirmed in 1982 by Lobene et al. (*Clinical Preventative Dentistry*, January–February (1982)) who showed no significant clinical difference on plaque and gingivitis scores. Similar results. i.e., no clinical difference between waxed and unwaxed floss with respect to reduced gingival inflammation were shown by Finkelstein in 1979 (*J. Dent. Res.*, vol. 58, pp. 1034–1039 (1979)). No differences in gingival health were shown by Wunderlich in 1981 (*J. Dent. Res.*, vol. 60A, p. 862 (1981)). No differences in plaque removal were reported by Schmidt et al. in 1962 (*J. Dent. Res.* (1962)) with flosses of various types. Stevens in 1980, studied floss with variable diameters and showed no difference in plaque and gingival health. Carter et al., *Va Dent. J.*, vol. 52, pp. 18–27 (1975), studied professional and self-administered waxed and unwaxed floss and found that both significantly reduced gingival bleeding of interproximal and gingival sulci. Unwaxed floss appeared slightly, but not significantly more effective.

In view of this clinical work, it is not surprising that most of the dental floss sold today is bonded and/or waxed. The "bonding" in the yarn industry today is used more to facilitate processing and production during floss manufacture and packaging than for "flossing" reasons. Since clinical tests show no difference between waxed and unwaxed floss, the floss industry has been comfortable with the yarn industry's propensity to use bonding agents in floss.

In any event, most people in the world do not floss their teeth. Instead, sticks or toothpicks are often used to clean their teeth.

Maetani et al, U.S. Pat. No. 2,504,228, describe a metallic dental casting coated with a PTFE coating. The PTFE coating is applied from a solution. The PTFE may also be applied from a suspension (an organosol) that may include other resins as well, such as, for example a silicone.

Lorch in U.S. Pat. No. 4,776,358 describes a flossing tape that carries its own supply of a dentifrice. The tape may be made of a confronting pair of laminae films that are microporous. The dentifrice is positioned between confronting surfaces of the two laminae, and the longitudinal opposite edges of the two laminae are sealed together. In use, the dentifrice flows out through the pores of the laminae. The laminae may be films of PTFE. The dentifrice is conventional, generally a commercially available material, Blass in U.S. Pat. No. 4,996,056 describes coating a dental floss or tape with a mixture of wax and PTFE powder.

La Rochelle in U.S. Pat. No. 4,157,386 discloses a lozenge which coats the surfaces of the teeth and which contains fluoride ion, a polishing agent, and a vegetable oil.

Gaffar et al in U.S. Pat. No. 5,344,641 discloses a dentifrice containing an antibacterial agent, an antibacterial enhancing agent, a polishing agent, and a solubilizing agent. The antibacterial enhancing agent is an anionic film-forming material thought to attach to tooth surfaces thereby preventing bacterial attachment and enhancing delivery of the antibacterial agent to tooth surfaces.

Raaf et al in U.S. Pat. No. 4,169,885 discloses a filled capsule which has an outer hydrophilic active substance and an inner core containing a hydrophobic substance, a fluoride source and an antimicrobial substance. Upon consumption of the capsule, the hydrophilic substance is believed to fix the hydrophobic active substance to the teeth.

Hill et al in U.S. Pat. No. 5,165,913 discloses dental floss which contains a surfactant, silicone and a chemotherapeutic agent. The chemotherapeutic agent is delivered upon splaying of the floss. The surfactant and the silicone are believed to coat the teeth, provide a smooth feeling to the user, and prevent the attachment of bacteria.

Chang in U.S. Pat. No. Re 31,787 discloses an elution reducing dentifrice containing a membrane-forming material. Application of the membrane-forming material is believed to inhibit the elution of a previously applied therapeutic agent (i.e., fluoride).

Curtis et al in U.S. Pat. No. 4,528,182 and Crawford et al in U.S. Pat. No. 4,490,353 disclose an antiplaque dentifrice composition containing a quaternary ammonium compound, a betaine surfactant, polyethylene glycol and an abrasive. The presence of the betaine surfactant is believed to increase the foaming of the dentifrice and to prevent the deactivating of the quaternary ammonium compound.

Published PCT application WO 93/20775 discloses compositions for coating surfaces, such as those of teeth, which contain particles of poly(fluoroethylene) coated with a cationic polyelectrolyte such as polyethyleneimine. However, this reference does not describe the use of a bifunctional transfer agent, which contains both functional groups which are compatible with hydrophobic barrier materials and functional groups which are electrostatically positively charged.

However, none of these approaches has proven to be satisfactory. Thus, there remains a definite need in the art for improved methods, compositions, and dental delivery systems which are effective for the prevention of bacterial adhesion to teeth and exhibit antimicrobial properties.

There also remains a need for compositions which can be effectively applied to teeth using a toothpick or dental stick and result in improved antimicrobial properties.

SUMMARY OF THE INVENTION

Accordingly, it is one object of the present invention to provide novel dental delivery systems which exhibit improved antimicrobial properties.

It is another object of the present invention to provide novel dental floss which exhibits improved antimicrobial properties.

It is another object of the present invention to provide novel toothpicks which exhibit improved antimicrobial properties.

It is another object of the present invention to provide a method for treating teeth which confers improved microbial resistance on the teeth.

It is another object of the present invention to provide a method for treating teeth which confers a prolonged microbial resistance on the teeth.

It is another object of the present invention to provide a method for treating teeth which results in a reduced ability of bacteria to adhere to teeth.

It is another object of the present invention to provide novel compositions which confer improved microbial resistance on teeth.

It is another object of the present invention to provide novel compositions which confer a prolonged microbial resistance on teeth.

It is another object of the present invention to provide novel compositions which result in a reduced ability of bacteria to adhere to teeth.

It is another object of the present invention to provide novel cationic surfactants useful in such methods, compositions, and dental delivery systems.

It is another object of the present invention to treat/coat dental surfaces with an enduring, inert, continuous, hydrophobic material which will constitute a physical barrier against access to the tooth surface by bacteria, acids, food remnants, etc., and prevent loss of fluorine by elution from dental surfaces.

It is another object of the present invention to provide such barriers, for deposition onto dental surfaces, which include materials which enhance the purposes of oral hygiene such as sources of fluoride, substances which are shown to inhibit the attachment, propagation, growth or colonization of undesirable bacteria, anti-septic or antibiotic materials, detergents, anti-inflammatories, and other such active agents.

These and other objects, which will become apparent during the following detailed description, have been achieved by the inventors' discovery that application of a composition which comprises:

(a) 1 to 20 wt. %, based on the total weight of (a) and (b), of a transfer agent; and (b) 80 to 99 wt. %, based on the total weight of (a) and (b), of a barrier material to teeth results in a prolonged reduction in the ability of bacteria to adhere to teeth.

Thus, the present invention provides new compositions which bond to substrates, especially to those dental (tooth) surfaces having pits, fissures, depressions, cracks, dental tubules, interstices or irregularities. The compositions conform to the topography of the surfaces of the teeth, depositing protective barrier materials on the surfaces of the teeth.

The methods of this invention result in the bonding of waxy materials to substrates, such as teeth. The application of the present compositions to dental floss or dental tape, according to the methods of the present invention, provides an appropriate combination of bonding to the floss or tape together with transferability of the compositions onto and into the surfaces of the teeth during use of the floss or tape.

The compositions of the present invention may be applied to dental surfaces using toothbrushes, both manual and automated, having either "natural", nylon, or other fibrous, multifilament or monofilament bristles. The methodology employed for applying the barrier materials and duplex films to the bristles may be as described below as used for application to dental flosses and tapes.

The compositions of the present invention may also be applied to dental surfaces using any of a variety of interdental or dental appliances of wood, plastic, metals, etc. A stick-like appliance may be covered at one or both ends with any material suitable for coating with the composition of the present invention. The appliance may be similar to the presently marketed interdental appliances of Johnson & Johnson known as "Stimudents", in a configuration similar to the popular cotton "Q-Tip" swabs, or in a configuration in which the applicator is inserted in or otherwise attached to an appropriate holder.

The materials used for covering the applicator-ends of the appliance may include, for example: a) natural or synthetic yarn, filaments, or other fibrous material either as such or assembled as a textile, or to any braided, stranded, woven, non-woven, knitted, matted, felted, etc. material, in which the materials of the composition of the present invention (hereinafter MCPI) are held among or between the fibers or the strands of the materials; b) foam-like or otherwise porous materials in which the MCPI are held within pores or apertures; or c) non-porous, non-fibrous materials such as some types of wood, plastic, metal, etc.

In the Examples, below, the surfaces of wooden toothpicks were coated and a film of MCPI transferred to the wet surfaces of glass microscope slides. The toothpicks were merely dipped and dried, using the same techniques as for dental floss.

Thus, in one embodiment of the present invention, the surfaces of the teeth are coated with a material which forms a "duplex film" composed of a strongly electrostatically-adhesive monolayer of a positively charged polyelectrolyte (such as, for example, polyethyleneimine, PEI) reacted with a monolayer of fatty acid molecules. The fatty acid molecules bond to the PEI layers with their carboxylic groups while the hydrocarbon parts of the fatty acid chains form a highly hydrophobic interface that is compatible with the hydrophobic barrier materials.

In addition to fatty acids, other compounds having low surface tensions and water repelling properties that can be used in the practice of the present invention include polymethylalkyl siloxanes such as, for example, polymethylhexadecylsiloxane, and polyfluoroalkyl methylsiloxanes (for example, polymethyl-3,3,3-trifluoropropyl siloxane). These further enhance the hydrophobicity of the duplex films and facilitate the transfer of hydrophobic barrier materials. Saturated hydrocarbons such as waxes, including beeswax, carnauba wax, and petroleum waxes such as the paraffins, and fluorocarbon polymers may also be used.

In other applications, the duplex film can be replaced by a single monolayer composed of a low molecular weight surfactant in which positively charged groups react with the surfaces of the teeth and the water repelling part of the chain forms a highly hydrophobic interface. Examples of such surfactants are cetyltrimethylammonium bromide (CTAB), hexadecyltrimethylammonium bromide (HDTAB), and various amines and quaternary amines, of which a good example is Hyamine-1622 quaternary amine.

The compositions of the present invention are generally semi-solid or solid state materials which may be applied to dental surfaces by dental floss, dental tape, interdental appliances, swabs, sticks, toothpicks and all other applicators or methods of application by which semi-solid or solid materials may be brought into contact with dental surfaces. All such applicators or methods of application are hereafter referred to as "Applicators".

As shown in the schematic illustrations given in FIGS. 1 and 2a and b, the compositions of the present invention, as applied to dental surfaces, provide a multi-stratum protective coating (hereafter called the "Protective Coating: or "PC"), as follows:

(1) The transfer agent stratum has dual functionality, being composed of materials having some molecular segments or parts of a polymeric chain which are positively charged and other such segments which exhibit hydrophobic characteristics.

Three categories of transfer agent materials include: (a) monomeric cationic surfactants, (b) cationic polyelectrolytes or their products or complexes with organic or inorganic acids, and (c) polypeptide-like materials having a preponderance of positively charged functional groups.

(2) Barrier Stratum: to the hydrophobic components of the transfer agent stratum, a hydrophobic, inert material (hereafter called the "barrier" material), such as a wax is adhered. The thickness of the barrier stratum is typically between about $1\mu$ and about $10\mu$.

In preferred embodiments the PC may further provide:

(3) Anti-Bacterial function: within the barrier stratum may be blended therapeutic, hygienic or otherwise desirable materials which are released as they are exposed on the surfaces of the barrier stratum. One of the materials typically blended into the barrier material is a substance or substances shown to inhibit the attachment or otherwise defeat the propagation, growth or colonization of deleterious bacteria such as *Streptococcus mutans, S. sobrinus*, etc. As noted above the composition may further comprise other active agents. Any such substance is referred to hereafter as an "Active-Agent" or "A-A" material.

Thus, the present invention makes possible the first significant improvement in consumer or home dental care in decades. Specifically, the present invention provides the following advances:

I. Application of a composition of the present invention to teeth provides a continuous, hydrophobic, inert barrier which prevents acids, staining materials, (FIG. 9 shows several staining materials on an untreated surface on the left, 9a, compared with the same materials on a surface treated with a composition of the present invention on the right, 9b), food particles, bacteria and all other materials from gaining access to the treated dental surface and thus provides protection against all of the usual destructive processes—including the loss of fluorine by elution. In addition, these deleterious substances attach themselves less readily to the barrier than they do to unprotected tooth surfaces.

II. Any bacteria or other debris which do attach to the protective barrier are easily removed by toothbrushing, pressure water cleaning, flossing and even, probably, by vigorous mouth rinsing since the amorphous barrier is easily cleaved or sheared, removing the outermost material but leaving some of its protective barrier remaining. Without such protection, bacteria which have attached themselves to the tooth surface soon become impossible to dislodge by toothbrushing or flossing and must be professionally removed. Since bacterial attachment begins to take place soon after each meal, the barrier is of great prophylactic significance.

III. The barrier material readily fills and thus seals pits, fissures and cracks which are the favorite venues for bacteria colonization and plaque development. The barrier remains in place until mechanically removed from these pits, etc. and thereby provides protection which is even more extended in the vulnerable areas, since the barrier material is not removed from pits, fissures, etc. as easily as it is from smoother tooth surfaces in the ordinary course of abrasive action by the tongue, mastication of food, toothbrushing, etc.

IV. By the addition to the barrier composition of an antibacterial material, 5-amino-1,3-bis(2-ethylhexyl)-5-methylhexahydropyrimidine, which is obtainable from Angus Chemical Co. under the trade name Hexetidine being an example of a most especially preferred active agent, bacterial attachment to the barrier surface is reduced by an estimated 90% or more, compared to the number and density of bacteria which attach to unprotected tooth surfaces. Of course, those bacteria which do attach are still easily removed by typical consumer activities such as toothbrushing and flossing. In addition, it appears that the hexetidine migrates or diffuses from the barrier material onto tooth surfaces which the barrier didn't reach, providing some protection to these hard to reach and most vulnerable areas.

V. Importantly, the benefits of the present invention can be delivered by a broad range of application methods, e.g., dental floss and tape, Q-tip®-like swabs, toothpicks, interdental appliances like Stimudents®, pre-coated toothbrushes, and any other applicators for consumer or professional use that one wishes to use. The only criterion is that it must be able to bring a waxy material into contact with dental surfaces.

Thus, application of the present compositions is effective to treat/coat dental surfaces with an enduring, inert, continuous, hydrophobic composition which constitutes a physical barrier against access to tooth surfaces by bacteria, acids, food remnants, etc., and prevents loss of fluorine by elution from dental surfaces. In addition, significantly fewer bacteria attach to the barrier than attach to unprotected tooth surfaces. More importantly, bacteria and other materials which attach to the barrier are easily removed by toothbrushing, dental flossing, pressure water cleaning and even vigorous mouth rinsing since the amorphous barrier material is readily cleaved or sheared with little effort. Even after the removal of such surface materials, barrier materials remain to continue to provide protection.

On application and thereafter, the barrier materials of the present invention are forced to conform to the topography of the dental surfaces on which they are applied. Especially important, the barrier materials fill the pits, fissures, cracks and other imperfections in dental surfaces, thus blocking those sites in which bacteria are most frequently found and from which they are most difficult to remove. And in such sites, the barrier materials are least subject to removal by the usual oral sources of abrasion and surfaces activities such as movements of the tongue, toothbrushing, mastication, etc. and thus provide the most enduring protection where it is most needed.

In a preferred embodiment the barrier material includes agents which enhance the purposes of oral hygiene such as substances which are: (a) shown to enhance the inhibition of attachment, propagation, growth or colonization of undesirable bacteria, (b) other germicidal, anti-septic or anti-biotic materials, (c) anti-inflammatories and (d), other desirable agents.

Using one of the most preferred embodiments of the present invention, in which a heterocyclic nitroparaffin-derived material, such as hexetidine, is blended into the barrier composition, bacterial attachment on the protective barrier is reduced by ≧90% as compared with unprotected tooth surfaces. Those few bacteria which may attach to the barrier surface are removable with gentle shearing action.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
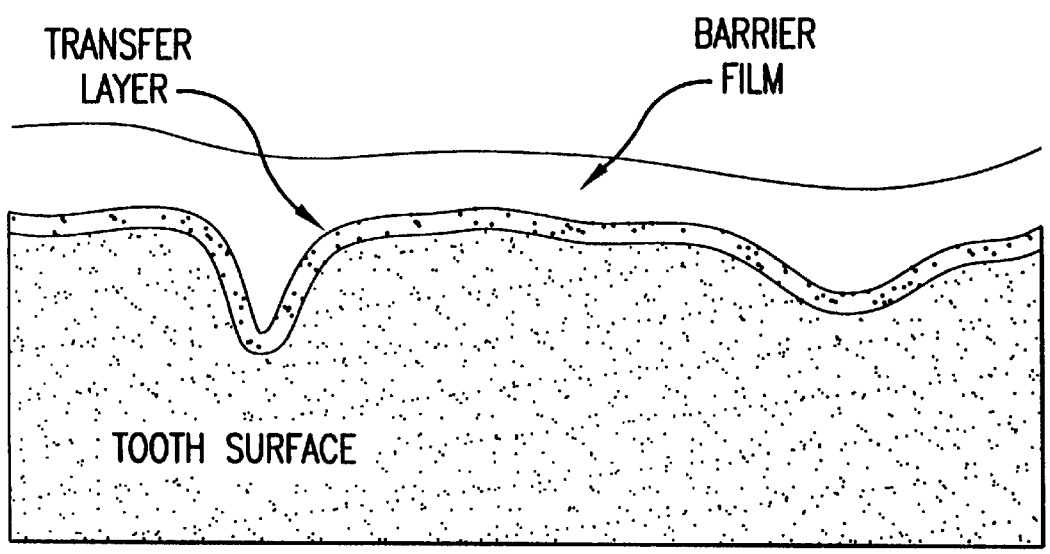
FIG. 1 is a partial section, taken in a horizontal plane, through a coated human tooth, showing the irregular tooth surface, the conformation of the coating to the tooth surface and its relative thickness, all on a much enlarged scale. The hydrophobic barrier film, containing antibacterial and other functional agents, conforms to the substrate and fills pits, fissures, cracks and other irregularities of the tooth surface. The transfer layer facilitates adhesion of the hydrophobic barrier film to the tooth surface.
Figure 2A:
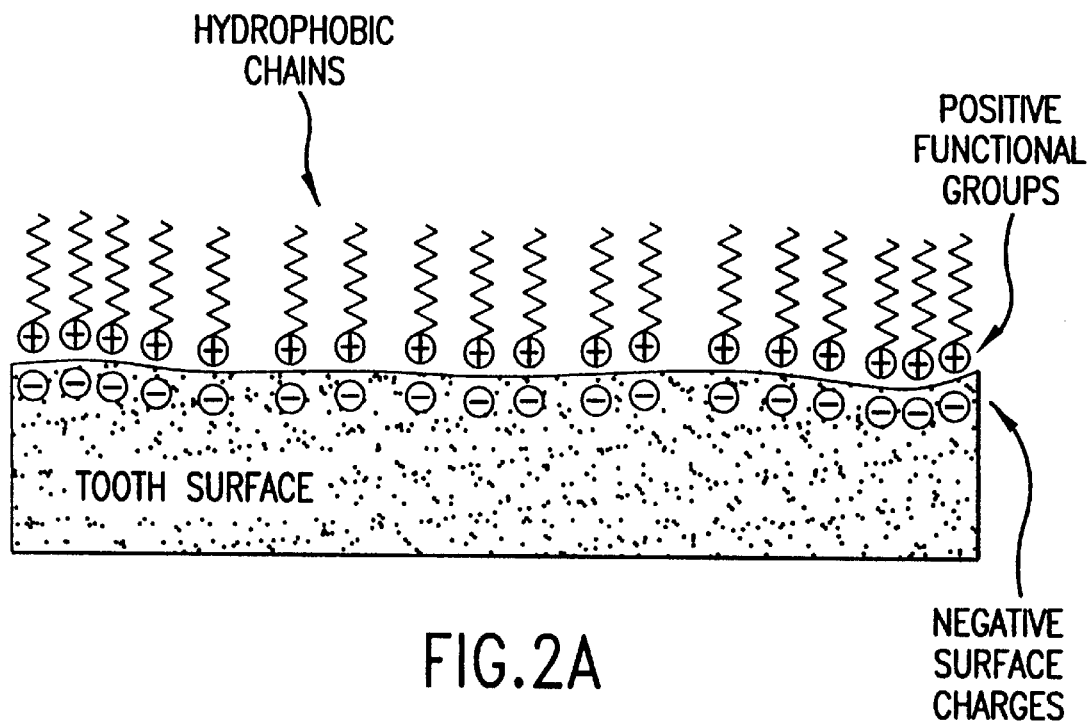
FIGS. 2a and b are enlarged views of the coated tooth surface, showing the area of the tooth surface in FIG. 1, to demonstrate the electrostatic charge distribution at the interface between the tooth surface and the transfer agent. This figures illustrates the mode of attachment of the transfer agent to the negatively charged tooth surface. (a) The molecules of the positively charged surfactant form a dense monolayer which attaches to the negatively charged substrate. The alkyl groups of the transfer agent face away from the surface. (b) Polyamine molecules adsorb to the substrate with their hydrophobic side groups facing away from the hydrophilic tooth surface.
Figure 2B:
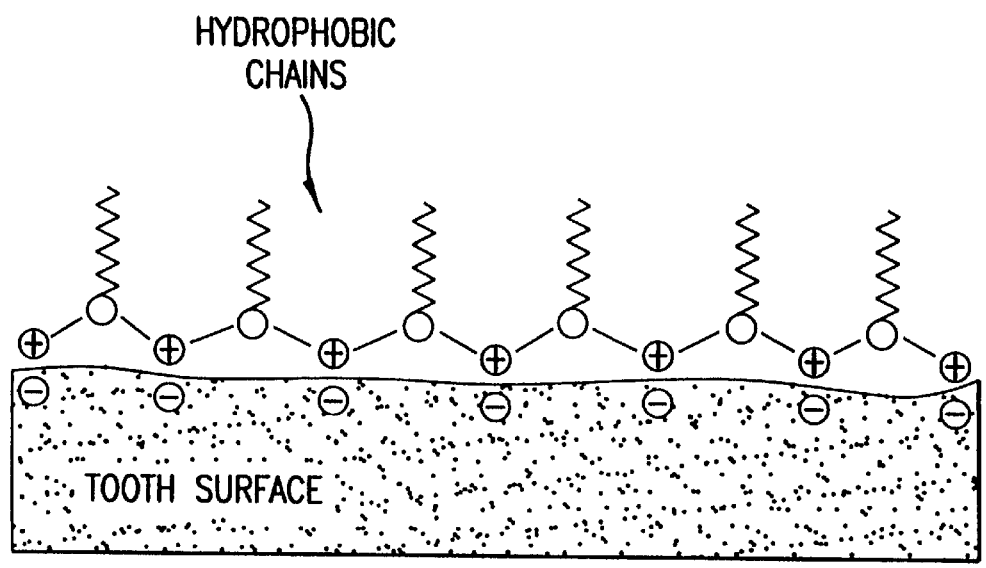

Thus, in a first embodiment, the present invention provides novel compositions which contain:

(a) 1 to 20 wt. %, based on the total weight of (a) and (b), of a transfer agent; and (b) 80 to 99 wt. %, based on the total weight of (a) and (b), of a barrier material.

Preferably, the present composition contains:

(a) 3 to 5 wt. %, based on the total weight of (a) and (b), of a transfer agent; and (b) 95 to 97 wt. %, based on the total weight of (a) and (b), of a barrier material.

The Transfer Agent Function

To adhere a hydrophobic barrier material to a wet, hydrophilic, negatively charged tooth surface, a bi-functional transfer agent material is employed. This material has some active groups which are electrostatically positively charged and some active groups which are compatible with the hydrophobic materials of the barrier stratum.

Useful transfer agent materials include various cetyl amine compounds, various diamines (including for example, Duomeens and Ethoduomeens), nitroparaffin-derived heterocyclic amines, and quaternary ammonium compounds. Also useful are compounds of certain cationic polyelectrolytes, invented for the purposes of the present invention and introduced herewith, including, for example, polyethyleneimine (PEI) derivatized with varying concentrations of fatty acids such as, for example, stearic acid, palmitic acid, oleic acid, etc.

Certain of these transfer agents also inhibit the attachment or otherwise defeat the propagation, growth or colonization of bacteria such as, for example, *Streptococcus mutans* and *Streptococcus sobrinus*, when added in appropriate concentrations so as to be able to function as a transfer agent and also perform the A-A function.

Some substances, notably some of the bifunctional amine hydrofluorides and specifically the quaternary ammonium fluorides have been used in prior art to produce a mono-layer of bi-polar material adhered to the dental surfaces as an end in itself. But experimentation suggests that the resulting single molecular layer is insufficient to provide a durable functional barrier against attachment of bacteria or to interdict access to tooth surfaces by acids, etc.

Transfer Agent Materials

Cationic transfer agent materials useful in the present invention are believed to attach to tooth surfaces via a complexing interaction between the cationic portion of the material and the proteinaceous portion of the tooth and thus predispose or condition the surface of the tooth so that a waxy material will then adhere to the surface. Surface active materials that are capable of strong bonding to the negatively charged and hydrophilic surfaces of human teeth include various straight-chain alkylammonium compounds, cyclic alkylammonium compounds, petroleum derived cationics, and polymeric cationic materials.

a) Straight-chain alkylammonium compounds

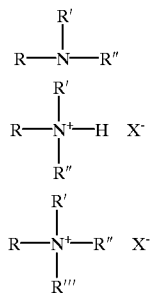

R represents a long ($C_{8-20}$) alkyl chain which may be substituted with one or more hydroxy groups, R', R", and R'" each independently may be either a long ($C_{8-20}$) alkyl chain which may be substituted with one or more hydroxy groups or a smaller ($C_{1-4}$) alkyl groups which may be substituted with one or more hydroxy groups or aryl ($C_{6-10}$) groups or hydrogen, and $X^-$ represents an anion such as chloride or fluoride. These schematic formulas are given for the purpose of defining the classes of compounds and represent the simplest concepts of cationic transfer agents whereby one or more hydrophobic alkyl groups are linked to a cationic nitrogen atom. In many instances the linkage is more complex as, for example, in $RCONHCH_2CH_2CH_2N(CH_3)_2$. In addition, cationic transfer agents may contain more than one cationic nitrogen atom such as the following class of compounds $RNHCH_2CH_2CH_2NH_2$ and derivatives thereof.

Representative examples of compounds according to the above formulas are:

cetyl trimethylammonium chloride (CTAB),
hexadecyltrimethylammonium bromide (HDTAB),
stearyl dimethylbenzylammonium chloride,
lauryl dimethylbenzylammonium chloride,
cetyl dimethylethylammonium halide,
cetyl dimethylbenzylammonium halide,
cetyl trimethylammonium halide,
dodecyl ethyldimethylammonium halide,
lauryl trimethylammonium halide,
coconut alkyltrimethylammonium halide,
N,N-$C_{8-20}$-dialkyldimethylammonium halide, and specifically compounds such as bis(hydrogenated tallow alkyl) dimethylammonium chloride which is known to adsorb onto the surface with hydrophobic groups oriented away from it, 2-hydroxydodecyl-2-hydroxyethyl dimethyl ammonium chloride and N-octadecyl-N,N',N'-tris-(2-hydroxyethyl)-1, 3-diaminopropane dihydrofluoride.

b) Cyclic Alkylammonium Compounds

A further preferred group of compounds of the present invention which have been found to be applicable includes a class of surface-active quaternary ammonium compounds in which the nitrogen atom carrying the cationic charge is part of a heterocyclic ring. Suitable compounds, for example, are as follows:

laurylpyridinium chloride or bromide,
tetradecylpyridinium bromide,
cetylpyridinium halide (chloride, bromide or fluoride).

c) Petroleum Derived Cationics

Typical basic amines are derived from petroleum-based raw materials such as olefins, paraffins, and aromatic hydrocarbons and include compounds with at least one aliphatic carbon chain containing six or more carbon atoms attached to the nitrogen. Thus, amine salts, diamines, amidoamines, alkoxylated amines, and their respective quaternary salts are applicable.

Preferred compounds of this type include tallow or coco alkyl substituted 1,3-propylene diamines sold by Witco under the trade names of "Adogen" and "Emcol" and similar diamines sold by Akzo under the trade name "Duomeen" and their polyethenoxy derivatives under the trade names of "Ethomeen" and "Ethoduomeens".

d) Polymeric Amines

Suitable polymeric amines comprise a class of polymers containing ionic groups along the backbone chain and exhibit properties of both electrolytes and polymers. These materials contain nitrogen, of primary, secondary, tertiary or quaternary functionality in their backbone and may have weight average molecular weights as low as about 100 or higher than about 100,000. Representative of these polymeric cationic transfer agents are the following:

polydimeryl polyamine (General Mills Chemical Co.),
polyamide (trade name "Versamide"),
polyacrylamides,
polydiallyldimethylammonium chloride ("Cat-Floc"),
polyhexamethylene biguanide compounds as sold under the trade name "Vantocil", and also other biguanides, for example those disclosed in U.S. Pat. Nos. 2,684,924, 2,990, 425, 3,183,230, 3,468,898, 4,022,834, 4,053,636 and 4,198, 425,
1,5-dimethyl-1,5-diazaundecamethylene polymethobromide ("Polybrene" from Aldrich),
polyvinylpyrrolidone and their derivatives,
polypeptides,
poly(allylamine) hydrochloride,
polyoxyethylenated amines, and specifically,
polyethyleneimine ("Polymin" from BASF), and a class of related and surface active cationic polymers prepared by converting a fraction of the amino groups to their acyl derivatives. The polyethyleneimine is first condensed with less than the stoichiometric quantity of acid halides thus alkylating some of the amino groups and the remaining amino groups are then condensed with hydrogen halides such as hydrogen chloride or, preferentially, hydrogen fluoride. The surface activity of these compounds vary with the number of amino groups which are acylated, and with the chain length of the acylating group RCO—. The condensation reaction is typically performed with stearic or oleic acid chlorides in the presence of a solvent containing metal fluoride, preferentially silver fluoride, in such a manner that silver chloride formed in the reaction precipitates from the solvent (see Example XV).

Also suitable, for the purpose of this invention, are cationic derivatives of polysaccharides such as dextran, starch or cellulose, for example, diethylaminoethyl cellulose ("DEAE-cellulose"). Examples of applicable copolymers based on acrylamide and a cationic monomer are available commercially under the trade name RETEN from Hercules Inc., or under the name FLOC AID from National Adhesives. Particular examples of such polymers are FLOC AID 305 and RETEN 220. Similarly useful are acrylamide-based polyelectrolytes as sold by Allied Colloids under the trade name PERCOL. Further examples of suitable materials are the cationic guar derivatives such as those sold under the trade name JAGUAR by Celanese-Hall.

A further preferred group of compounds which comprises a class of water-insoluble polymers, having nitrogen atoms in their molecules, are quaternary polymers of quaternary ammonium type, betaine type, pyridylpyridinium type or vinylpyridinium-type. Examples are as follows;

poly(vinyl-benzylmethyllaurylammonium chloride),
poly(vinyl-benzylstearylbetaine),
poly(vinyl-benzyllaurylpyridylpyridinium chloride),
poly(vinyl-benzylcetylammonylhexyl ether) and quaternized polyoxyethyleneated long chain amines, with the general formula $RN(CH_3)[(C_2H_4O)_xH]_2(+) A(-)$, where A(−) is generally chloride or fluoride, x is a number from 1 to 20, and R is $C_{8-22}$-alkyl.

These cationic materials, by reacting with dental surfaces, produce strongly hydrophobic films onto which hydrophobic barrier materials are easily transferred by rubbing, smearing, or burnishing.

It is important that the reason for this transferability be understood. The surfaces of human teeth are normally hydrophilic, negatively charged, and are "lubricated" by a hydrated biofilm composed of bacteria and other bioorganisms. The transfer and adhesion of the barrier materials onto such dental surfaces is difficult or practically impossible unless the biofilm is modified by a material that is hydrophobic and therefore compatible with the barrier materials.

In a preferred embodiment, the transfer agent, a cationic surfactant, is a polymer which contains a nitrogen atom in a repeating unit and in which a portion of the nitrogen atoms are quaternized by formation of a salt with a $C_{8-20}$ fatty acid, preferably a $C_{12-20}$ fatty acid. Examples of such polymeric cationic surfactants include polyacrylamides, polyvinylpyridines, or polyamines, e.g., poly (ethyleneimine), in which from 5 to 95 mole %, preferably 40 to 60 mole %, of the nitrogen atoms have been quaternized by formation of a salt with a fatty acid. Typically such polymers will have a weight average molecular weight of 600 to 60,000, preferably 600 to 1,800.

In a particularly preferred embodiment, the cationic surfactant is a polymer which contains a nitrogen atom in a repeating unit and in which a first portion of the nitrogen atoms are quaternized with a $C_{8-20}$ fatty acid, preferably a $C_{12-20}$ fatty acid, and a second portion of the nitrogen atoms are quaternized by forming a salt with HF. Examples of such polymeric cationic surfactants include polyacrylamides, polyvinylpyridines or polyamines, e.g., poly (ethyleneimine), in which from 5 to 95 mole %, preferably from 40 to 60 mole %, of the nitrogen atoms are converted to their acid derivatives by reaction with stearic or oleic acid chlorides, and from 5 to 95 mole %, preferably from 40 to 60 mole %, of the nitrogen atoms are quaternized with HF. In this case, the polymeric cationic surfactant will have a weight average molecular weight of 600 to 60,000, preferably 600 to 1,800.

In another preferred embodiment, the cationic surf actant is a $C_{8-20}$-alkylamine which has been quaternized with HF, such as cetylamine hydrofluoride.

The Barrier Function

Now having a mechanism for adhering a protective, hydrophobic material to the hydrophilic dental substrate, any of several barrier materials may be selected to perform this function. A microcrystalline wax, for example, is a component in a barrier composition which provides an adherent, conformal, hydrophobic, continuous, inert, colorless or near-colorless barrier which, on application and with subsequent smearing or disturbance, is forced into pits, fissures, cracks and other irregularities of tooth surfaces, thus blocking those sites most vulnerable to occupation by undesirable bacteria and other debris. This waxy barrier appears to endure in place and function indefinitely or until it is mechanically removed. Thus, with the transfer and barrier functions performed, extended protection is provided against deleterious activities since the treated dental surfaces are entirely sealed against bacteria, acids, staining materials, loss of dental fluorine, etc.

In use, the barrier material is rubbed, on application and thereafter, into pits, cracks, concavities and other depressions. Importantly, barrier materials are amorphous materials which shear or cleave easily so that materials which may adhere to the surface of the barrier may be removed easily by the application of moderate shear forces such as are applied by the action of the tongue against dental surfaces, toothbrushing, dental flossing, forced water cleaning or vigorous mouth rinsing. This same low-shear characteristic moves the barrier materials about, exposing any active agent substances blended into the barrier materials.

Hydrophobic Barrier Materials

It has been found that various hydrophobic compounds of high molecular weight, solid at body temperature and generally similar to fats and oils are useful as barrier forming materials. Typically they are long chain hydrocarbons, especially normal paraffins having a chain length of 16 carbons or greater, paraffins with several loci of branching and unsaturation, where the extent of such branching and unsaturation does not create unacceptable toxicity nor lower the solidification point below body temperature, and show essentially no solubility in water or saliva. The major types of these wax-like materials belong to two basic categories:

I. Natural waxes of animal, vegetable or mineral origin such as beeswax, lanolin, spermaceti, carnauba wax, petroleum waxes including paraffin waxes and microcrystalline petrolatum; and II. Synthetic materials including ethylenic polymers such as "Carbowax", polymethylene wax ("Paraflint") and various hydrocarbon types as obtained via Fisher-Tropsch synthesis.

Other suitable materials include silicone-based polymers such as polymethylalkylsiloxane, polydimethylsiloxane, poly(perfluoroalkylmethyl siloxane), poly(methyl-3,3,3-trifluoropropyl siloxane) and various aromatic (phenyl containing) siloxanes as sold by Petrarch, which is now United Chemical.

Also useful are various fluoropolymers where some or all of the hydrogen is replaced by fluorine, including, among others: polytetrafluoroethylene (PTFE); fluorinated polyethylene-propylene (FEP); polyvinylidene fluoride (PVDF); and polyvinylfluoride (PVF).

These polymers can be applied to a dental appliance as aqueous or non-aqueous dispersions.

In another embodiment, the present composition contains:

(a') 1 to 10 wt. %, preferably 2 to 5 wt. %, based on the total weight of (a'), (b'), and (c'), of a transfer agent;

(b') 70 to 98 wt. %, preferably 85 to 93 wt. %, based on the total weight of (a'), (b'), and (c'), of a barrier material; and (c') 1 to 20 wt. %, preferably 5 to 10 wt. %, based on the total weight of (a'), (b'), and (c'), of an active agent.

The Active-Agent (A-A) Function

Experimentation with the technology of the present invention demonstrates that some types of materials inhibit or defeat the attachment and/or propagation, growth or colonization of bacteria on dental surfaces. The bacteria with which the experiments were performed, *Streptococcus mutans*, and *Streptococcus sobrinus*, are shown to be major sources of bacterial plaque colonies and their sequelae.

Among the materials which demonstrably perform the A-A function are various cetyl amines, nitroparaffin derivatives, duomeens, ethoxylated duomeens, and other quaternary ammonium compounds. Especially useful is 5-Amino-1,3-bis(2-ethylhexyl)-5-methylhexahydropyrimidine, such as is obtainable from Angus Chemical Co. by the tradename hexetidine.

In addition, the innovative materials whose novel benefits and compositions are described and claimed for the first time in this disclosure/application are useful as Active Agents. These include polyethyleneimines to which fatty acids such as oleic acid, etc. have been added.

Some of the A-A materials tested and described in the Examples below migrated out or diffused away from the areas on which a Protective Coating was applied so that, to some extent, the A-A function extended to areas not reached by the PC itself.

These A-A materials may be blended into the barrier material so that, as the barrier material is sheared, cleaved, disturbed, eroded, abraded, etc., fresh A-A material is exposed and freed to function.

Active Agent Materials

Various compounds which possess antibacterial activity (i.e. are germicides) can be used in compositions of the present invention to counter bacterial attachment and plaque formation. Examples of applicable antimicrobial agents belong to the following types.

a) Amine-free compounds halogenated salicylanilides, as described in U.S. Pat. No. 5,344,641, including:

4',5-dibromosalicylanilide
3,4',5-trichlorosalicylanilide
3,4',5-tribromosalicylanilide
2,3,3',5-tetrachlorosalicylanilide
3,3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoromethyl salicylanilide (fluorophene)

| Benzoic Esters | |
|---|---|
| Methyl | p-Hydroxybenzoic Ester |
| Ethyl | p-Hydroxybenzoic Ester |
| Propyl | p-Hydroxybenzoic Ester |
| Butyl | p-Hydroxybenzoic Ester | halogenated diphenyl ethers, as described in U.S. Pat. No. 5,344,641, including:

2',4,4'-trichloro-2-hydroxy-diphenyl ether (Triclosan)
2,2'-dihydroxy-5,5'-dibromo-diphenyl ether.

halogenated carbanilides, as described in U.S. Pat. No. 5,344,641, including:

3,4,4'-trichlorocarbanilide
3-trifluoromethyl-4,4'-dichlorocarbanilide
3,3,4'-trichlorocarbanilide Also included are phenolic compounds, representative examples of which are described in U.S. Pat. No. 5,290,541, which includes phenol, its derivatives and bisphenolic compounds. Specifically, they include:

| Phenol and its Homologs | |
|---|---|
| Phenol | -Phenol |
| 2 Methyl | -Phenol |
| 3 Methyl | -Phenol |
| 4 Methyl | -Phenol |
| 4 Ethyl | -Phenol |
| 2,4-Dimethyl | -Phenol |
| 2,5-Dimethyl | -Phenol |
| 3,4-Dimethyl | -Phenol |
| 2,6-Dimethyl | -Phenol |
| 4-n-Propyl | -Phenol |
| 4-n-Butyl | -Phenol |
| 4-n-Amyl | -Phenol |
| 4-tert-Amyl | -Phenol |
| 4-n-Hexyl | -Phenol |
| 4-n-Heptyl | -Phenol |
| 2-Methoxy-4-(2-Propenyl)-Phenol (Eugenol) | |
| 2-Isopropyl-5-Methyl-Phenol (Thymol) | |

Mono- and Poly-Alkyl and Aralkyl Halophenols

| Methyl | -p-Chlorophenol |
|---|---|
| Ethyl | -p-Chlorophenol |
| n-Propyl | -p-Chlorophenol |
| n-Butyl | -p-Chlorophenol |
| n-Amyl | -p-Chlorophenol |
| sec-Amyl | -p-Chlorophenol |
| n-Hexyl | -p-Chlorophenol |
| Cyclohexyl | -p-Chlorophenol |
| n-Heptyl | -p-Chlorophenol |
| n-Octyl | -p-Chlorophenol |
| O-Chlorophenol | |
| Methyl | -o-Chlorophenol |
| Ethyl | -o-Chlorophenol |
| n-Propyl | -o-Chlorophenol |
| n-Butyl | -o-Chlorophenol |
| n-Amyl | -o-Chlorophenol |
| tert-Amyl | -o-Chlorophenol |
| n-Hexyl | -o-Chlorophenol |
| n-Heptyl | -o-Chlorophenol |
| p-Chlorophenol | |
| o-Benzyl | -p-Chlorophenol |
| o-Benzyl-m-methyl | -p-Chlorophenol |
| o-Benzyl-m,m-dimethyl | -p-Chlorophenol |

-continued

| | |
|---|---|
| o-Phenylethyl | -p-Chlorophenol |
| o-Phenylethyl-m-methyl | -p-Chlorophenol |
| 3-Methyl | -p-Chlorophenol |
| 3,5-Dimethyl | -p-Chlorophenol |
| 6-Ethyl-3-methyl | -p-Chlorophenol |
| 6-n-Propyl-3-methyl | -p-Chlorophenol |
| 6-iso-Propyl-3-methyl | -p-Chlorophenol |
| 2-Ethyl-3,5-dimethyl | -p-Chlorophenol |
| 6-sec-Butyl-3-methyl | -p-Chlorophenol |
| 2-iso-Propyl-3,5-dimethyl | -p-Chlorophenol |
| 6-Diethylmethyl-3-methyl | -p-Chlorophenol |
| 6-iso-Propyl-2-ethyl-3-methyl | -p-Chlorophenol |
| 2-sec-Amyl-3,5-dimethyl | -p-Chlorophenol |
| 2-Diethylmethyl-3,5-dimethyl | -p-Chlorophenol |
| 6-sec-Octyl-3-methyl | -p-Chlorophenol |
| p-Bromophenol | |
| Methyl | -p-Bromophenol |
| Ethyl | -p-Bromophenol |
| n-Propyl | -p-Bromophenol |
| n-Butyl | -p-Bromophenol |
| n-Amyl | -p-Bromophenol |
| sec-Amyl | -p-Bromophenol |
| n-Hexyl | -p-Bromophenol |
| cyclohexyl | -p-Bromophenol |
| o-Bromophenol | o-Bromophenol |
| tert-Amyl | o-Bromophenol |
| n-Hexyl | o-Bromophenol |
| n-Propyl-m,m-dimethyl | |
| 2-Phenyl phenol | |
| 4-Chloro-2-methyl phenol | |
| 4-Chloro-3-methyl phenol | |
| 4-Chloro-3,5-dimethyl phenol | |
| 2,4-Dichloro-3,5-dimethyl phenol | |
| 3,4,5,6-Tetrabromo-2-methylphenol | |
| 5-Methyl-2-pentylphenol | |
| 4-Isopropyl-3-methylphenol | |
| 5-Chloro-2-hydroxydiphenyl methane | |
| Resorcinol and its Derivatives | |
| Resorcinol | |
| Methyl | -Resorcinol |
| Ethyl | -Resorcinol |
| n-Propyl | -Resorcinol |
| n-Butyl | -Resorcinol |
| n-Amyl | -Resorcinol |
| n-Hexyl | -Resorcinol |
| n-Heptyl | -Resorcinol |
| n-Octyl | -Resorcinol |
| n-Nonyl | -Resorcinol |
| Phenyl | -Resorcinol |
| Benzyl | -Resorcinol |
| Phenylethyl | -Resorcinol |
| Phenylpropyl | -Resorcinol |
| p-Chlorobenzyl | -Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |

Bisphenol A
2,2'-methylene bis(4-chlorophenol)
2,2'-methylene bis(3,4,6-trichlorophenol) (hexachlorophene)
2,2'-methylene bis(4-chloro-6-bromophenol)
bis(2-hydroxy-3,5-dichlorophenyl)sulfide
bis(2-hydroxy-5-chlorobenzyl)sulfide b) Amine-containing compounds (mostly quaternary amines) Among the most common of these antibacterial quaternary ammonium compounds are:

alkyldimethylbenzylammonium chloride benzethonium chloride (Hyamine 1622), diisobutylphenoxyethoxyethyl dimethyl benzyl ammonium chloride, and cetyl pyridinium halides (chloride, bromide, iodide, and fluoride).

Other materials of this nature are also mentioned in: U.S. Pat. Nos. 2,984,639, 3,325,402, 3,431,208, and 3,703,583, and British Pat. No. 1,319,396.

Further analogous compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Typical examples are: dodecyl trimethyl ammonium bromide, and benzyl dimethyl stearyl ammonium chloride.

Preferred antimicrobial materials useful in the present invention belong to the nitroparaffia-in-derived heterocyclic class of compounds. Examples of such compounds may be classified into the following types:

monocyclic oxazolidines, bicyclic oxalidines, polymeric bicyclic oxalidines, 1,3-dioxanes, oxazolines, oxazolidinones, and hexahydropyrimidines [5-amino-1,3-bis(2-ethylhexyl)-5-methyl hexahydropyrimidine which is sold under the trade name "hexetidine" by Angus Chemical Co.].

Other guanine-based antimicrobial substances are:

1,6-bis-(p-chlorophenyldiguanidine)hexane, also known by the trade name "chlorhexidine", 1,6-di-(2-ethylhexyldiguanidine)hexane known as "alexidine", and 1,1'-hexamethylene-bis-{5-(4-fluorophenyl)-diguanidine} also known as "fluorhexidine".

In a preferred embodiment of this invention, a non-aqueous dispersion containing micro-crystalline wax, paraffin oil and hexetidine was prepared. The resulting mixture was applied to a polyamide dental tape by drawing the tape through the dispersion. After drying, the tape was drawn over extracted human teeth and glass rods. Testing and observation evidenced that a substantial, smooth and continuous coating of a waxy barrier film had been applied both to the surfaces of the teeth and the glass rods.

The film was also transferred when the dental and glass surfaces were wetted with water immediately prior to the treatment. The hydrophobic films of applied material were not removed by brushing them with ten strokes of a toothbrush while submerged in water.

As alluded to above, the present compositions may further comprise a source of fluoride, such as sodium fluoride, potassium fluoride, tin fluoride, zinc fluoride, organic fluorides such as long-chained aminofluorides, for example oleylaminofluoride, cetyl aminofluoride or ethanolaminohydrofluoride, fluorosilicates, for example, potassium hexafluorosilicate or sodium hexafluorosilicate, fluorophosphates such as ammonium, sodium, potassium, magnesium or calcium fluorophosphate and/or fluorozirconates, for example sodium, potassium or tin fluorozirconate. The present compositions may also further comprise one or more antibiotics, such as penicillin, polymyxin B, vancomycin, kanamycin, erythromycin, niddamycin, metronidazole, spiramycin and tetracycline.

The present compositions may be prepared by a method in which the barrier material is first suspended or dissolved in an appropriate solvent (e.g. xylene, toluene, petroleum ether, methanol, ethanol, or where, for example, aqueous dispersions of fluorocarbons are selected as barrier materials, water). The transfer agent and, optionally, active agent(s) are then added and the solvent removed by, e.g., evaporation.

The present dental delivery systems may be prepared by coating a suitable substrate (dental floss, toothbrush, toothpick, etc.) with the present composition. This may conveniently be carried out by dipping the substrate in the suspension or solution containing the barrier material, transfer agent, and optionally, active agent referred to above in connection with the preparation of the present compositions, and then drying the substrate to remove the solvent, leaving a coating of the present composition on the substrate. Alternatively, the dry composition prepared above may be redissolved or resuspended, and the substrate dipped in the thus-formed solution or suspension, followed by solvent removal.

The present method of protecting the teeth may be carried out by contacting the present dental delivery system with the teeth to effect transfer of the composition from the dental delivery system to the surface of the teeth. The exact means of contacting will depend of course on the nature of the dental delivery system. Thus, in the case of a dental floss, flossing will suffice, while brushing will suffice, in the case of a toothbrush. Rubbing will be appropriate for both toothpicks and cotton swabs.

Other features of the invention will become apparent in the course of the following descriptions of exemplary embodiments which are given for illustration of the invention and are not intended to be limiting thereof.

EXAMPLES

In the following examples, and throughout this specification, all parts and percentages are by weight, and all temperatures are in degrees Celsius, unless expressly stated to be otherwise. Where the solids content of a dispersion or solution is reported, it expresses the weight of solids based on the total weight of the dispersion or solution, respectively. Where a molecular weight is specified, it is the molecular weight range ascribed to the product by the commercial supplier, which is identified. Generally this is believed to be weight average molecular weight.

In all of the following examples in which teeth are mentioned, the teeth are extracted human teeth which were professionally cleaned with abrasives, sterilized by multiple autoclaving and, prior to use in the following examples, hydrated in distilled water for at least one hour. Immediately prior to use the teeth were immersed in and withdrawn from a mixture of distilled water and fresh human saliva (at approximately 1:1 by volume), so that the treated surfaces were wet at the time of application of materials.

Example I

Figure 3:
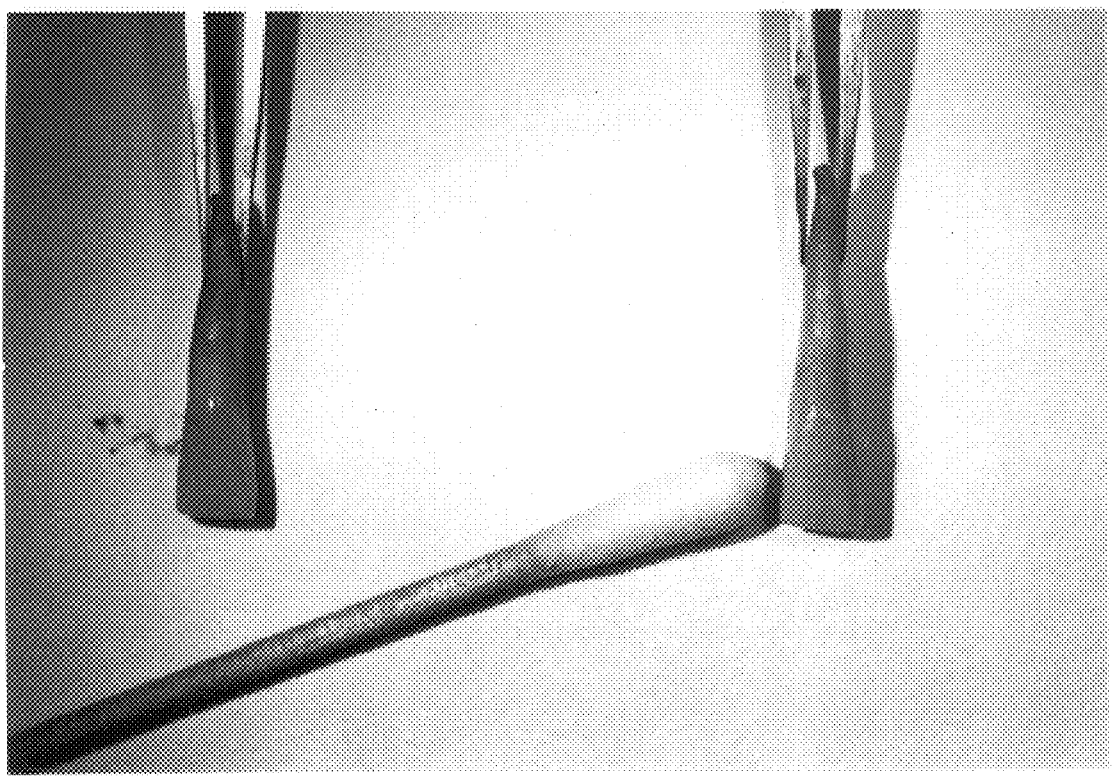
FIG. 3 shows the application of a composition according to the present invention to a tooth by a cotton swab.

43 Grams of xylene solvent sold by EM Science, 5 grams of microcrystalline wax sold by Calwax under the trade designation Victory White and 2 grams of paraffin oil, Saybolt viscosity 340–355, sold by EM Science, were heated to approx. 50° C. and vigorously mixed until a clear solution was produced. The mixture was allowed to cool to room temperature and 0.125 grams of N-tallow-1,3-propanediamine sold by Akzo under the trade designation Duomeen TDO (as transfer agent) were admixed by stirring. The result was a mixture in which the microcrystalline wax appeared to be uniformly dispersed but not dissolved in the solvent. A cotton tipped applicator was dipped into this mixture and the solvent was allowed to evaporate at an elevated temperature of about 50° C. The coated applicator was then rubbed against a tooth surface until a smooth and water-repelling film was obtained, the tooth surface having been wetted with a 1:1 by volume mixture of distilled water and fresh human saliva immediately prior to the application of the coated applicator (see FIG. 3).

In order to determine the degree of hydrophobicity imparted by the waxy film, drops of water were deposited on the surface of the film and their contact angles were measured. Repeated measurements showed values in excess of 90° indicating a strong tendency of the surface to repel water.

In vitro Demonstration of Efficacy

The bacteria adsorption-inhibiting ability of each formulation thus obtained was evaluated as follows: A pure culture of bacteria obtained from American Type Culture Collection (ATCC), (designated ATCC # 27607, and identified as *Streptoccocus sobrinus*, the same organisms having also and previously been designated and identified as *Streptoccocus mutans*), was maintained by subculturing onto fresh brain-heart-infusion agar plates and incubating in a $CO_2$ incubator at 37° C. To prepare a testing medium, a small quantity of bacteria was transferred into 4 ml of brain-heart infusion (BHI) liquid medium (obtained from Curtin Matheson) and incubated for 24 hours at 37° C. After the incubation period, the concentration of the bacteria in the inoculum was adjusted, with sterilized BHI medium, to about $2 \times 10^7$ cells/ml ($OD_{560}$=0.02). The contact bacteria solution (0.3 ml) of the above was added to 30 ml of BHI medium containing 4% sucrose and shaken at 120 strokes/minute for 3 minutes. The tested samples of untreated teeth and teeth coated with the transfer film were then placed into the inoculated medium and incubated under anaerobic conditions at 37° C. for 48 hours. After removal from the medium, the teeth were rinsed in water and stained with Crystal Violet stain. Examination by microscopy revealed significant inhibition of bacterial adherence in the areas covered by the transferred films as compared with the untreated control surfaces which were covered by heavy deposits of adherent bacteria.

Example II

Figure 7:
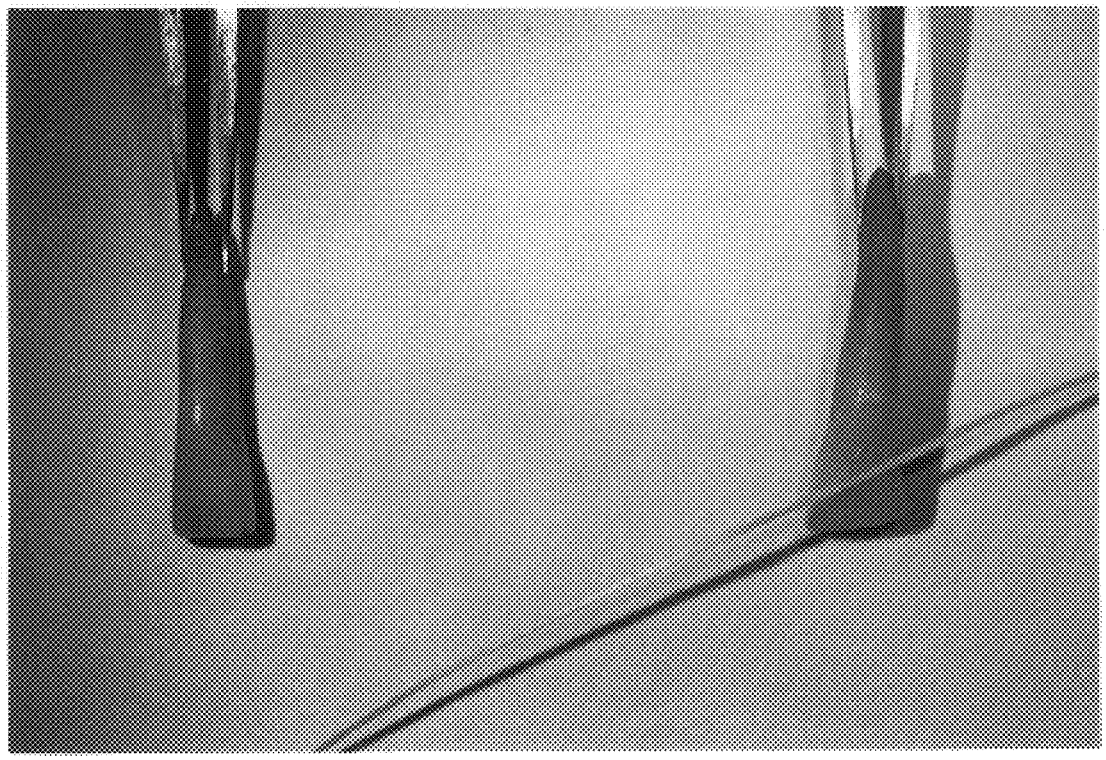
FIG. 7 shows the application of a composition according to the present invention to a tooth by dental floss.

A mixture was prepared as described in Example I. A polyamide dental floss, as manufactured for Johnson & Johnson, Inc., was drawn through and vertically out of the mixture at a rate of about 3 mm per second, the thickness of the coating being controlled by the rate at which the floss was drawn through the mixture. Following air drying at an elevated temperature, a short strand of the floss, approx. 2 feet in length, was drawn back and forth across the tooth surfaces (extracted human central incisors), imitating a normal flossing procedure, until a uniform and tenaciously adhering film was produced (see FIG. 7). The film exhibited a high degree of hydrophobicity as attested by measurements of contact angles in excess of 90°. Adherence of bacteria to the tooth surfaces was evaluated according to the procedure outlined in Example I. A significant inhibition of bacterial adherence to the transferred film was observed.

Example III

A mixture was prepared as described in Example I. Wooden toothpicks were immersed in the mixture and slowly withdrawn. After drying at room temperature, toothpicks were rubbed over wetted extracted tooth surfaces until a smooth and continuous film was formed. Further, in order to determine the degree of hydrophobicity imparted by the waxy film, drops of water were deposited on a film surface. Repeated measurements of the contact angles showed values in excess of 90° indicating a high degree of hydrophobicity of the interface. Exposure of the treated teeth to the bacteria media for 48 hours or more demonstrated a significant reduction in bacteria adsorption, comparable to the reduction observed in Examples I and II.

Example IV

Figure 5:
FIG. 5 shows the application of a composition according to the present invention to a tooth by a toothbrush.

A mixture was prepared as described in Example I. Ordinary toothbrushes, some of the bristles of which were "natural" fibers, and some nylon, were immersed in the mixture and withdrawn at a rate of about 3 mm/sec. After drying at an elevated temperature, the toothbrushes were drawn back and forth several times over the tooth surfaces, simulating the action and movement of toothbrushing (see FIG. 5).

Treated surfaces of the teeth were then observed by microscope. Substantial, smooth and continuous layers of the deposited waxy material appeared on the tooth surfaces. Further, in order to determine the degree of hydrophobicity imparted by the waxy films, drops of water were deposited on the transferred films and the contact angles measured. Repeated measurements showed values in excess of 90° indicating the high degree of hydrophobicity of the surfaces. A significant inhibition of bacterial adherence to the transferred film was observed.

Example V

43 Grams of xylene solvent sold by EM Science, 5 grams of microcrystalline wax sold by Calwax under the trade designation Victory White and 2 grams of paraffin oil, Saybolt viscosity 340–355, sold by EM Science, were heated to approx. 50° C. and vigorously mixed until a clear solution was produced. The mixture was allowed to cool to room temperature. Then, 0.2 grams of cetyl amine sold by Aldrich (as transfer agent) were admixed by stirring. The result was a mixture in which the microcrystalline wax appeared to be uniformly dispersed but not completely dissolved in the solvent. A cotton tipped applicator was dipped into this mixture and withdrawn, and the solvent was allowed to evaporate at an elevated temperature. The coated applicator was then rubbed against the wetted glass slide until a smooth and water-repelling film was obtained.

In order to determine the degree of hydrophobicity imparted by the waxy film, drops of water were deposited on the surface of the film and the contact angles were measured. Repeated measurements showed values in excess of 90° indicating a strong tendency of the surface to repel water.

Adherence of bacteria to the tooth surfaces was evaluated according to the procedure outlined in Example I. A significant inhibition of bacterial adherence to the barrier film was observed.

Example VI

A mixture was prepared as described in Example V. A polyamide dental floss, as manufactured for Johnson & Johnson, Inc., was drawn through and vertically out of the mixture at a rate of about 3 mm per second, the thickness of the coating being controlled by the rate at which the floss was drawn through the mixture. Following air drying at an elevated temperature, a short strand of the floss, approx. 2 feet in length, was drawn back and forth across the tooth surfaces, imitating a normal flossing procedure, until a uniform and tenaciously adhering film was produced. The film exhibited a high degree of hydrophobicity as attested by measurements of contact angles in excess of 90°. Adherence of bacteria to the tooth surfaces was evaluated according to the procedure outlined in Example I. A significant inhibition of bacterial adherence to the barrier film was observed.

Example VII

A mixture was prepared as described in Example V. Wooden toothpicks were immersed in the mixture and slowly withdrawn. After drying at room temperature, the toothpicks were rubbed repeatedly over wetted tooth surfaces until a smooth and continuous film was formed. Further, in order to determine the degree of hydrophobicity imparted by the waxy film, drops of water were deposited on the film surface and the contact angles were measured. Repeated measurements showed values in excess of 90° indicating a high degree of hydrophobicity of the interface. Exposure of the treated teeth to bacterial media resulted in a significant reduction in bacteria adsorption comparable to the reduction observed in Examples V and VI.

Example VIII

A mixture was prepared as described in Example V. Ordinary toothbrushes, some of the bristles of which "natural" fibers, and some nylon, were immersed in the mixture and slowly withdrawn. After drying at an elevated temperature, the toothbrushes were drawn back and forth several times over wetted tooth surfaces, simulating the action and movement of toothbrushing. The treated surfaces of the teeth were then observed by microscope. Substantial, smooth and continuous layers of the deposited waxy material appeared on the tooth surfaces. Further, in order to determine the degree of hydrophobicity imparted by the waxy films, drops of water were deposited on the transferred films and the contact angles measured. Repeated measurements showed values in excess of 90° indicating the high degree of hydrophobicity of the surfaces. Incubation for 48 hours in bacterial media showed a significant inhibition of bacterial adherence. Further, it was noted that subsequent brushing, while both the tooth and toothbrush were immersed in water, resulted in complete removal of bacteria from the waxy film while the surrounding untreated areas remained covered by bacterial colonies.

Enhancement of the Inhibition of Bacterial Attachment and/or Propagation, Growth and Colonization A significant enhancement in efficacy of the barrier film to inhibit adherence of bacterial colonies was realized when various antibacterial agents such as hexetidine, for example, were incorporated into the formulation. Examples IX through XII demonstrate the effectiveness of this approach.

Example IX

43 Grams of xylene solvent sold by EM Science, 5 grams of microcrystalline wax sold by Calwax under the trade designation Victory White and 2 grams of paraffin oil, Saybolt viscosity 340–355, sold by EM Science, were heated to approx. 50° C. and vigorously mixed until a clear solution was produced. The mixture was allowed to cool to room temperature. Then, 0.3 grams of Duomeen TDO (AKZO Chemical Co.) (as transfer agent) were admixed by stirring. To this mixture, 1.25 grams of 5-Amino-1,3-bis(2-ethylhexyl)-5-methylhexahydropyrimidine sold by Angus Chemical Co., under the trade designation of hexetidine (as active agent) was added with vigorous mixing. The result was a mixture in which the microcrystalline wax appeared to be uniformly dispersed but not dissolved. A cotton tipped applicator was dipped into this mixture, and the solvent was allowed to evaporate from it at an elevated temperature. The coated applicator was then rubbed against a glass slide until a smooth and water-repelling film was obtained, the slide having been wetted with distilled water immediately prior to the application of the applicator.

In order to determine the degree of hydrophobicity imparted by the waxy film, drops of water were deposited on the surface of the film and their contact angles were measured. Repeated measurements showed values in excess of 90° indicating a strong tendency of the surface to repel water. The ability of the barrier film to inhibit adsorption of bacteria was evaluated as described in Example I. A negligible number of bacterial colonies, as compared with the untreated control areas adjacent to the film were observed even after 4 days exposure to the bacteria bearing media.

Example X

Figure 8A:
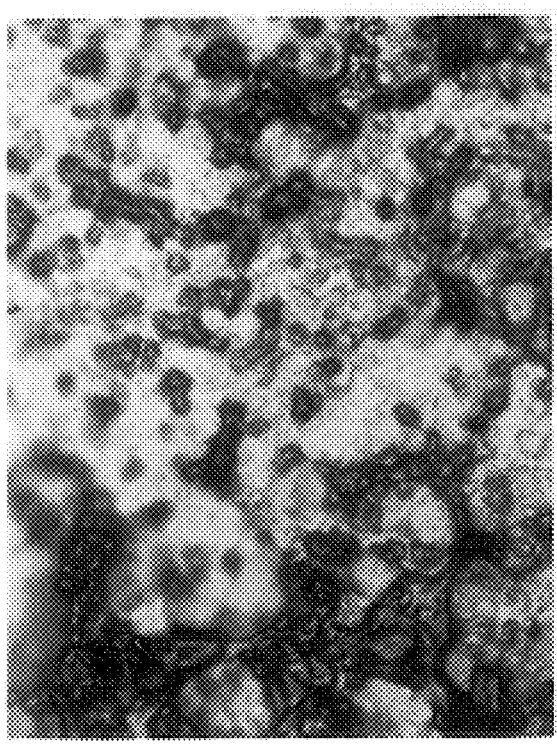
FIGS. 8a and b are photomicrographs of an untreated tooth (FIG. 8a) and a tooth treated according to the present invention (FIG. 8b) after exposure to bacteria-rich media for 48 hours.
Figure 8B:
Figure 9A:
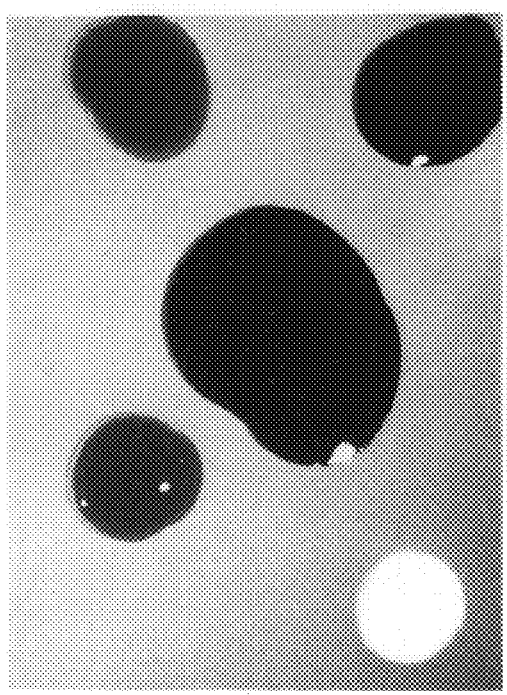
FIGS. 9a and b show the appearance of staining materials on an untreated glass slide (FIG. 9a) and a slide treated according to the present invention (FIG. 9b).
Figure 9B:
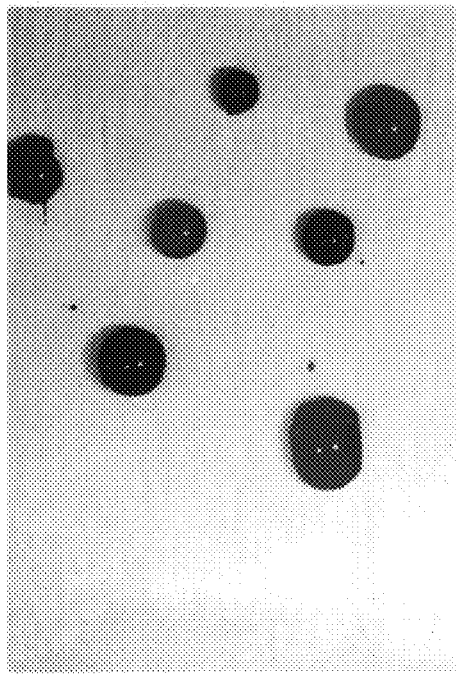

A mixture was prepared as described in Example IX. A polyamide dental floss, as manufactured for Johnson & Johnson, Inc., was drawn through and vertically out of the mixture at a rate of about 3 mm per second, the thickness of the coating being controlled by the rate at which the floss was drawn through the mixture. Following air drying at an elevated temperature, a short strand of the floss, approx. 2 feet in length, was drawn back and forth across tooth surfaces (human central incisors), imitating a normal flossing procedure, until a uniform and tenaciously adhering film was produced. The film exhibited a high degree of hydrophobicity as attested by measurements of contact angles in excess of 90°. Adherence of bacteria to the treated tooth surfaces was evaluated according to the procedure outlined in Example I. Examination by microscopy (FIGS. 8a and 8b) revealed that the area covered by the transferred film was essentially free of bacterial colonies while the surrounding non-treated control areas were covered by heavy deposits of adsorbed bacteria.

Example XI

A mixture was prepared as described in Example IX. Wooden toothpicks were immersed in the mixture and withdrawn. After drying at room temperature, toothpicks were rubbed repeatedly over wetted tooth surfaces until a smooth and continuous film was formed. Further, in order to determine the degree of hydrophobicity imparted by the waxy film, drops of water were deposited on the film surface and the contact angles measured. Repeated measurements showed values in excess of 90° indicating a high degree of hydrophobicity of the interface. Exposure of the treated teeth to bacterial media resulted in a negligible amount of isolated bacterial colonies adhering to the film surface.

Example XII

Figure 6A:
FIGS. 6a and b are photomicrographs of an untreated tooth (FIG. 6a) and a tooth treated according to the present invention (FIG. 6b) after exposure to bacteria-rich media for 48 hours.
Figure 6B:

A mixture was prepared as described in Example IX. ordinary toothbrushes, some of the bristles of which were "natural" fibers, and some nylon, were immersed in the mixture and slowly withdrawn. After drying at an elevated temperature, the toothbrushes were drawn back and forth several times over wetted tooth surfaces, simulating the action and movement of toothbrushing. The treated surfaces of the teeth were then observed by microscope. Substantial, smooth and continuous layers of the deposited waxy material appeared on the tooth surfaces. Further, in order to determine the degree of hydrophobicity imparted by the waxy films, drops of water were deposited on the transferred films and the contact angles were measured. Repeated measurements showed values in excess of 90° indicating the high degree of hydrophobicity of the surfaces. Incubation for 48 hours in bacterial media showed a high resistance of the film to react with any components of the media including bacteria (FIGS. 6a and 6b). Microscopic observations failed to detect any residual bacteria or bacterial colonies after the treated tooth surfaces were gently brushed with a toothbrush under running tap water.

Example XIII 83.5 Grams of xylene solvent sold by EM Science, 10 grams of microcrystalline wax sold by Calwax under the trade designation Victory White and 4 grams of paraffin oil, Saybolt viscosity 340–355, sold by EM Science, were heated to approximately 50° C. and vigorously mixed until a clear solution was produced. The mixture was allowed to cool to room temperature. To this mixture, 2.5 grams of 5-amino-1,3-bis(2-ethylhexyl)-5-methylhexahydropyrimidine sold by Angus Chemical Co., under the trade designation of hexetidine (as transfer agent and active agent) was added with vigorous mixing. The result was a mixture in which the microcrystalline wax appeared to be uniformly dispersed but not completely dissolved. A cotton tipped applicator was dipped into this mixture, and the solvent was allowed to evaporate at an elevated temperature (40–50° C.). The cotton applicator was then rubbed against tooth surfaces until a smooth and water-repelling film was obtained.

In order to determine the degree of hydrophobicity imparted by the waxy film, drops of water were deposited on the surface of the film and contact angles were measured. Repeated measurements showed values in excess of 90° indicating a strong tendency of the surface to repel water.

Figure 4A:
FIGS. 4a and b are photomicrographs of an untreated tooth (FIG. 4a) and a tooth treated according to the present invention (FIG. 4b) after exposure to bacteria-rich media for 48 hours.
Figure 4B:

Adherence of bacteria to the treated surfaces was evaluated according to the procedure outlined in Example I. Examination by microscopy showed that treated surface areas of teeth were essentially free of adsorbed bacteria while untreated control surfaces were laden with heavy deposits of adhered bacterial colonies (FIGS. 4a and 4b).

Example XIV 84.75 Grams of xylene solvent sold by EM Science, 10 grams of microcrystalline wax sold by Calwax under the trade designation Victory White and 4 grams of paraffin oil, Saybolt viscosity 340–355, sold by EM Science, were heated to approximately 50° C. and vigorously mixed until a clear solution was produced. The mixture was allowed to cool to room temperature. To this mixture, 1.25 grams of N-tallow-1,3-propanediamine dioleate sold by Akzo Nobel Chemicals Inc., under the trade designation of Duomeen TDO (as transfer agent and active agent) was added with vigorous mixing. The result was a mixture in which the microcrystalline wax appeared to be uniformly dispersed but not completely dissolved. A cotton tipped applicator was dipped into this mixture and the solvent was allowed to evaporate at an elevated temperature (40–50° C.). The cotton applicator was then rubbed against a glass slide until a smooth and water-repelling film was obtained.

In order to determine the degree of hydrophobicity imparted by the waxy film, drops of water were deposited on the surface of the film and contact angles were measured. Repeated measurements showed values in excess of 90° indicating a strong tendency of the surface to repel water.

Adherence of bacteria to the barrier film was evaluated according to the procedure outlined in Example I. A significant inhibition of bacterial adherence to the barrier film was observed.

Example XV 4.3 Grams of polyethyleneimine (1/10 segmental molecular weight) and 15.2 grams of stearyol chloride (1/20 mol)

are dissolved in 25 ml of ethanol and refluxed gently for 30 minutes. After cooling to room temperature, 25 ml of 25% aqueous solution of silver fluoride is added and the mixture is stirred for 10 minutes. The precipitated silver chloride is filtered off, and the crude derivative is purified by crystallization. The crystalline derivative is transferred to a plastic beaker and dissolved in 25 ml of ethanol. 3.0 Grams of 40% hydrofluoric acid (1/20 mol+20%) are added to the solution and the whole is then evaporated on a water bath until its consistency is paste-like. The remaining solvent is driven out in vacuo at about 50° C. The compound remains as a colorless slightly brownish paste. It is soluble in alcohols and hydrocarbon-based solvents.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed as new and desired to be secured by Letters Patent of the United States is:

1. A composition, comprising:
   (a) 1 to 20 wt. %, based on the total weight of (a) and (b), of a transfer agent; and
   (b) 80 to 99 wt. %, based on the total weight of (a) and (b), of a barrier material;
   wherein said transfer agent is selected from the group consisting of compounds of the formulae (I), (II), and (III):

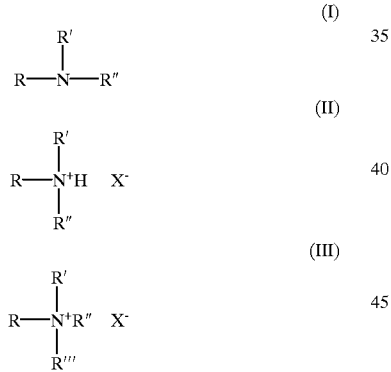

wherein R is a $C_{8-20}$ alkyl chain which may be substituted with one or more hydroxy groups, R', R", and R'" each independently are a $C_{8-20}$ alkyl chain which may be substituted with one or more hydroxy groups, a $C_{1-4}$ alkyl group which may be substituted with one or more hydroxy groups, a $C_{6-10}$ aryl group, or hydrogen, and X is fluoride or chloride; laurylpyridinium chloride; laurylpyridinium bromide; cetylpyridinium chloride; cetylpyridinium bromide; cetylpyridinium fluoride; petroleum derived cationics; polydimeryl polyamines; polydiallyl dimethylammonium chlorides, polyhexamethylene biguanides; 1,5-dimethyl-1,5-diazaundecamethylene polymethobromide; polyvinylpyrrolidones; polypeptides; poly(allylamine) hydrochloride; polyoxyethylenated amines; acylated polyethyleneimines; diethylaminoethyl cellulose; poly (vinyl-benzylstearylbetaine); poly(vinyl-benzylmethyllaurylammonium chloride); poly(vinyl-benzyllaurylpyridylpyridinium chloride); poly(vinyl-benzylcetylammonylhexyl ether); compounds of the formula $RN(CH_3)[(C_2H_4O)_xH]_2(+) A(-)$, where $A(-)$ is chloride or fluoride, X is a number from 1 to 20, and R is a $C_{8-22}$ alkyl group; polyacrylamide in which 5 to 95 mole % of the nitrogen atoms have been derivatized by reaction with a $C_{8-20}$ fatty acid halide and 5 to 95 mole % of the nitrogen atoms have been quaternized with HF; polyvinylpyridine in which 5 to 95 mole % of the nitrogen atoms have been derivatized by reaction with a $C_{8-20}$ fatty acid halide and 5 to 95 mole % of the nitrogen atoms have been quaternized with HF; and 5-amino-1,3-bis(2-ethylhexyl)-5-methylhexahydropyrimidine; and wherein said barrier material is selected from the group consisting of beeswax, lanolin, spermaceti, carnauba wax, paraffin waxes, microcrystalline waxes, petrolatum waxes, ethylenic polymer waxes, polymethylene waxes, polymethylalkylsiloxane, polydimethylsiloxane, poly(perfluoroalkylmethyl siloxane), poly(methyl-3,3,3-trifluoropropyl siloxane), polytetrafluoroethylene, fluorinated polyethylene-propylene, polyvinylidene fluoride, and polyvinylfluoride, wherein, when said composition is applied to a surface of a tooth, said composition forms a coating on said surface of said tooth in which said transfer agent binds electrostatically to said surface of said tooth and said barrier material binds to said transfer agent electrostatically bound to said surface of said tooth, and said coating conforms to and fills pits, fissures, cracks, and irregularities present on said surface of said tooth.

2. The composition of claim 1, comprising 3 to 5 wt. %, based on the total weight of (a) and (b), of said transfer agent and 95 to 97 wt. %, based on the total weight of (a) and (b), of said barrier material.

3. The composition of claim 1, wherein said barrier material is a microcystalline wax.

4. The composition of claim 1, wherein said transfer agent is 5-amino-1,3-bis(2-ethylhexyl)-5-methylhexahydropyrimidine.

5. The composition of claim 1, wherein said transfer agent is 5-amino-1,3-bis(2-ethylhexyl)-5-methylhexahydropyrimidine and said barrier material is a microcrystalline wax.

6. The composition of claim 1, comprising 3 to 5 wt. %, based on the total weight of (a) and (b), of 5-amino-1,3-bis (2-ethylhexyl)-5-methylhexahydropyrimidine and 95 to 97 wt. %, based on the total weight of (a) and (b), of a microcrystalline wax.

7. The composition of claim 1, further comprising paraffin oil.

8. A composition, comprising:
   (a') 1 to 10 wt. %, based on the total weight of (a'), (b'), and (c') of a transfer agent;
   (b') 70 to 98 wt. %, based on the total weight of (a'), (b'), and (c') of a barrier material; and
   (c') 1 to 20 wt. %, based on the total weight of (a'), (b'), and (c'), of an active agent;
   wherein said transfer agent is selected from the group consisting of compounds of the formulae (I), (II), and (III):

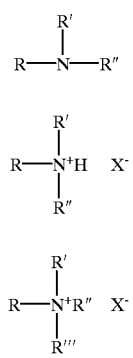

wherein R is a $C_{8-20}$ alkyl chain which may be substituted with one or more hydroxy groups, R', R", and R'" each independently are a $C_{8-20}$ alkyl chain which may be substituted with one or more hydroxy groups, a $C_{1-4}$ alkyl group which may be substituted with one or more hydroxy groups, a $C_{6-10}$ aryl group, or hydrogen, and X is fluoride or chloride; laurylpyridinium chloride; laurylpyridinium bromide; cetylpyridinium chloride; cetylpyridinium bromide; cetylpyridinium fluoride; petroleum derived cationics; polydimeryl polyamines; polydiallyl dimethylammonium chlorides, polyhexamethylene biguanides; 1,5-dimethyl-1,5-diazaundecamethylene polymethobromide; polyvinylpyrrolidones; polypeptides; poly(allylamine) hydrochloride; polyoxyethylenated amines; acylated polyethyleneimines; diethylaminoethyl cellulose; poly(vinyl-benzylstearylbetaine); poly(vinyl-benzylmethyllaurylammonium chloride); poly(vinyl-benzyllaurylpyridylpyridinium chloride); poly(vinyl-benzylcetylammonylhexyl ether); compounds of the formula $RN(CH_3)[(C_2H_4O)_xH]_2(+) A(-)$, where $A(-)$ is chloride or fluoride, X is a number from 1 to 20, and R is a $C_{8-22}$ alkyl group; polyacrylamide in which 5 to 95 mole % of the nitrogen atoms have been derivatized by reaction with a $C_{8-20}$ fatty acid halide and 5 to 95 mole % of the nitrogen atoms have been quaternized with HF; polyvinylpyridine in which 5 to 95 mole % of the nitrogen atoms have been derivatized by reaction with a $C_{8-20}$ fatty acid halide and 5 to 95 mole % of the nitrogen atoms have been quaternized with HF; and 5-amino-1,3-bis(2-ethylhexyl)-5-methylhexahydropyrimidine;

wherein said barrier material is selected from the group consisting of beeswax, lanolin, spermaceti, carnauba wax, paraffin waxes, microcrystalline waxes, petrolatum waxes, ethylenic polymer waxes, polymethylene waxes, polymethylalkylsiloxane, polydimethylsiloxane, poly(perfluoroalkylmethyl siloxane), poly(methyl-3,3,3-trifluoropropyl siloxane), polytetrafluoroethylene, fluorinated polyethylenepropylene, polyvinylidene fluoride, and polyvinylfluoride; and wherein said active agent is selected from the group consisting of 4',5-dibromosalicylanilide,
3,4',5-trichlorosalicylanilide,
3,4',5-tribromosalicylanilide,
2,3,3',5-tetrachlorosalicylanilide,
3,3,3',5-tetrachlorosalicylanilide,
3,5-dibromo-3'-trifluoromethyl salicylanilide,
5-n-octanoyl-3'-trifluoromethyl salicylanilide,
3,5-dibromo-4'-trifluoromethyl salicylanilide,
3,5-dibromo-3'-trifluoromethyl salicylanilide
methyl p-hydroxybenzoic ester,
ethyl p-hydroxybenzoic ester,
propyl p-hydroxybenzoic ester,
butyl p-hydroxybenzoic ester,
2',4,4'-trichloro-2-hydroxy-diphenyl ether,
2,2'-dihydroxy-5,5'-dibromo-diphenyl ether,
3,4,4'-trichlorocarbanilide,
3-trifluoromethyl-4,4'-dichlorocarbanilide,
3,3,4'-trichlorocarbanilide,
Phenol
2-methyl-phenol,
3-methyl-phenol,
4-methyl-phenol,
4-ethyl-phenol,
2,4-dimethyl-phenol,
2,5-dimethyl-phenol,
3,4-dimethyl-phenol,
2,6-dimethyl-phenol,
4-n-propyl-phenol,
4-n-butyl-phenol,
4-n-amyl-phenol,
4-tert-amyl-phenol,
4-n-hexyl-phenol,
4-n-heptyl-phenol,
2-methoxy-4-(2-propenyl)-phenol,
2-isopropyl-5-methyl-phenol,
methyl-p-chlorophenol,
ethyl-p-chlorophenol,
n-propyl-p-chlorophenol,
n-butyl-p-chlorophenol,
n-amyl-p-chlorophenol,
sec-amyl-p-chlorophenol,
n-hexyl-p-chlorophenol,
cyclohexyl-p-chlorophenol,
n-heptyl-p-chlorophenol,
n-octyl-p-chlorophenol,
methyl-o-chlorophenol,
ethyl-o-chlorophenol,
n-propyl-o-chlorophenol,
n-butyl-o-chlorophenol,
n-amyl-o-chlorophenol,
tert-amyl-o-chlorophenol,
n-hexyl-o-chlorophenol,
n-heptyl-o-chlorophenol,
o-benzyl-p-chlorophenol,
o-benzyl-m-methyl-p-chlorophenol,
o-benzyl-m,m-dimethyl-p-chlorophenol,
o-phenylethyl-p-chlorophenol,
o-phenylethyl-m-methyl-p-chlorophenol,
3-methyl-p-chlorophenol,
3,5-dimethyl-p-chlorophenol,
6-ethyl-3-methyl-p-chlorophenol,
6-n-propyl-3-methyl-p-chlorophenol,
6-iso-propyl-3-methyl-p-chlorophenol,
2-ethyl-3,5-dimethyl-p-chlorophenol,
6-sec-butyl-3-methyl-p-chlorophenol,
2-iso-propyl-3,5-dimethyl-p-chlorophenol,
6-diethylmethyl-3-methyl-p-chlorophenol,
6-iso-propyl-2-ethyl-3-methyl-p-chlorophenol,
2-sec-amyl-3,5-dimethyl-p-chlorophenol,
2-diethylmethyl-3,5-dimethyl-p-chlorophenol,
6-sec-octyl-3-methyl-p-chlorophenol,
methyl-p-bromophenol,
ethyl-p-bromophenol, n-propyl-p-bromophenol,
n-butyl-p-bromophenol,
n-amyl-p-bromophenol,
sec-amyl-p-bromophenol,
n-hexyl-p-bromophenol,
cyclohexyl-p-bromophenol,
tert-amyl-o-bromophenol,
n-hexyl-o-bromophenol,
n-propyl-m,m-dimethyl-o-bromophenol,
2-phenylphenol,
4-chloro-2-methylphenol,
4-chloro-3-methylphenol,
4-chloro-3,5-dimethylphenol,
2,4-dichloro-3,5-dimethylphenol,
3,4,5,6-tetrabromo-2-methylphenol,
5-methyl-2-pentylphenol,
4-isopropyl-3-methylphenol,
5-chloro-2-hydroxydiphenylmethane,
resorcinol
methyl-resorcinol,
ethyl-resorcinol,
n-propyl-resorcinol,
n-butyl-resorcinol,
n-amyl-resorcinol,
n-hexyl-resorcinol,
n-heptyl-resorcinol,
n-octyl-resorcinol,
n-nonyl-resorcinol,
phenyl-resorcinol,
benzyl-resorcinol,
phenylethyl-resorcinol,
phenylpropyl-resorcinol,
p-chlorobenzyl-resorcinol,
5-chloro-2,4-dihydroxydiphenylmethane,
4'-chloro-2,4-dihydroxydiphenylmethane,
5-bromo-2,4-dihydroxydiphenylmethane,
4'-bromo-2,4-dihydroxydiphenylmethane,
2,2'-methylene bis(4-chlorophenol),
2,2'-methylene bis(3,4,6-trichlorophenol),
2,2'-methylene bis(4-chloro-6-bromophenol),
bis(2-hydroxy-3,5-dichlorophenyl)sulfide,
bis(2-hydroxy-5-chlorobenzyl)sulfide,
benzethonium chloride,
diisobutylphenoxyethoxyethyl dimethyl benzyl ammonium chloride,
cetyl pyridinium chloride,
cetyl pyridinium bromide,
cetyl pyridinium iodide,
cetyl pyridinium fluoride,
dodecyl trimethyl ammonium bromide,
benzyl dimethyl stearyl ammonium chloride,
monocyclic oxazolidines,
bicyclic oxalidines,
polymeric bicyclic oxalidines,
1,3-dioxanes, oxazolines,
oxazolidinones,
5-amino-1,3-bis(2-ethylhexyl)-5-methyl hexahydropyrimidine,
1,6-bis-(p-chlorophenyldiguanidine)hexane,
1,6-di-(2-ethylhexyldiguanidine)hexane,
1,1'-hexamethylene-bis-{5-(4-fluorophenyl)-diguanidine},
sodium fluoride, potassium fluoride, tin fluoride, zinc fluoride, oleylaminofluoride, cetyl aminofluoride, ethanolaminohydrofluoride, potassium hexafluorosilicate, sodium hexafluorosilicate,
sodium fluorophosphate,
ammonium fluorophosphate,
potassium fluorophosphate,
magnesium fluorphosphate,
calcium fluorophosphate,
sodium fluorozirconate,
potassium fluorozirconate,
tin fluorozirconate,
penicillin, polymyxin B, vancomycin, kanamycin, erythromycin, niddamycin, metronidazole,
spiramycin, and tetracycline, wherein, when said composition is applied to a surface of a tooth, said composition forms a coating on said surface of said tooth in which said transfer agent binds electrostatically to said surface of said tooth and said barrier material binds to said transfer agent electrostatically bound to said surface of said tooth, and said coating conforms to and fills pits, fissures, cracks, and irregularities present on said surface of said tooth.

9. The composition of claim 8, comprising 2 to 5 wt. %, based on the total weight of (a'), (b'), and (c'), of said transfer agent and 85 to 93 wt. %, based on the total weight of (a'), (b'), and (c') , of said barrier material and 5 to 10 wt. %, based on the total weight of (a'), (b'), and (c'), of said active agent.

10. The composition of claim 8, wherein said barrier material is a microcystalline wax.

11. The composition of claim 8, wherein said transfer agent is 5-amino-1,3-bis(2-ethylhexyl)-5-methylhexahydropyrimidine.

12. The composition of claim 8, wherein said active agent is chlorhexidine.

13. The composition of claim 8, wherein said transfer agent is 5-amino-1,3-bis(2-ethylhexyl)-5-methylhexahydropyrimidine and said barrier material is a microcrystalline wax.

14. The composition of claim 8, wherein said transfer agent is 5-amino-1,3-bis(2-ethylhexyl)-5-methylhexahydropyrimidine and said active agent is chlorhexidine.

15. The composition of claim 8, wherein said barrier material is a microcrystalline wax and said active agent is chlorhexidine.

16. The composition of claim 8, wherein said transfer agent is 5-amino-1,3-bis(2-ethylhexyl)-5-methylhexahydropyrimidine, said barrier material is a microcrystalline wax, and said active agent is chlorhexidine.

17. The composition of claim 8, comprising 2 to 5 wt. %, based on the total weight of (a'), (b'), and (c'), of is 5-amino-1,3-bis(2-ethylhexyl)-5-methylhexahydropyrimidine; 85 to 93 wt. %, based on the total weight of (a'), (b'), and (c') , of a microcrystalline wax; and 5 to 10 wt. %, based on the total weight of (a'), (b'), and (c'), of chlorhexidine.

18. The composition of claim 8, further comprising paraffin oil.

* * * * *